United States Patent

Parle-Schmitz

[11] Patent Number: 6,159,483
[45] Date of Patent: Dec. 12, 2000

[54] STABILIZED LIQUID AQUEOUS COMPOSITION

[75] Inventor: Elizabeth K. Parle-Schmitz, Somerville, N.J.

[73] Assignee: Colgate-Palmolive Company, New York, N.Y.

[21] Appl. No.: 09/192,252

[22] Filed: Nov. 13, 1998

Related U.S. Application Data

[60] Provisional application No. 60/087,534, Jun. 1, 1998.

[51] Int. Cl.⁷ ............................. A61K 7/00; A61K 7/075; A61K 7/08; A61K 7/50
[52] U.S. Cl. .................. 424/401; 424/70.21; 424/70.24; 424/70.19; 510/151; 510/152; 510/155
[58] Field of Search .................................. 424/400, 401, 424/70.21, 75.24, 75.19; 510/152, 151, 155, 460, 424, 426

[56] References Cited

U.S. PATENT DOCUMENTS

| | | | |
|---|---|---|---|
| 5,312,559 | 5/1994 | Kacher et al. | 252/125 |
| 5,441,732 | 8/1995 | Hoeg et al. | 424/78.04 |
| 5,496,488 | 3/1996 | Kacher et al. | 252/125 |
| 6,008,173 | 12/1999 | Chopra et al. | 510/152 |

FOREIGN PATENT DOCUMENTS

| | | |
|---|---|---|
| WO93/08787 | 5/1993 | European Pat. Off. |
| 0604848A2 | 7/1994 | European Pat. Off. |
| 0663208A2 | 7/1995 | European Pat. Off. |
| WO96/17916 | 6/1996 | European Pat. Off. |
| WO96/37588 | 11/1996 | European Pat. Off. |
| 9309761 | 5/1993 | WIPO |
| 9716168 | 5/1997 | WIPO |

*Primary Examiner*—Shelley A. Dodson
*Attorney, Agent, or Firm*—Martin B. Barancik

[57] ABSTRACT

A liquid aqueous composition comprising:
(a) a skin cleansing effective amount of a surfactant or mixture thereof;
(b) a silicone fluid in quantities of from about 0.1 to about 8 wt % of the composition;
(c) a hydrocarbonaceous material in quantities of from about 0.1 to about 8 wt % of the composition;
(d) a cationic polymer in quantities of from about 0.02 to about 1 wt % of the composition;
(e) a combination of a hydroxy alkyl cellulose and a copolymer of a long chain alkylacrylate monomer and one or more monomers of acrylic acid, methacylic acid and one or more of a methyl, ethyl or propyl ester of said acid(s) wherein the copolymer is crosslinked with an allylic ether of a polyol, said combination in sufficient quantities to bring about a stabilized composition as visually evaluated, and
(f) the remainder water.

17 Claims, No Drawings

STABILIZED LIQUID AQUEOUS COMPOSITION

This application is a continuation-in-part of copending provisional patent application Ser. No. 60/087534 filed Jun. 1, 1998.

BACKGROUND OF THE INVENTION

Basic skin cleansing activities have been long addressed by the personal care industry. Removing soil from the skin is a worldwide requirement of the consumer population that has been met by the available skin cleansing products. The consumer population is now looking for additional benefits beyond basic cleansing. Skin conditioning i.e. smoothness, texture, etc., is a desired characteristic and brought about through the presence of emollients in a basic skin cleansing composition. Additionally, the presence of components which bring about an antibacterial effect on the skin are now becoming ever more acceptable and desirable by the consumer population.

Delivering a benefit to the skin other than cleansing during the cleansing process has been receiving increasing attention in the last few years. For example, the disclosure of dual compartment delivery systems to deliver benefit agents to the skin as well as larger sized droplets of the benefit agent are now known. However, in order to achieve these results the composition must be compatibilized, as assessed by stability parameters over a period of time and a range of temperatures. Such parameters include maintenance of visual phase integrity and viscosity. These parameters are particularly significant for liquid compositions wherein the large quantity of water make the establishment of a stable composition more difficult, particularly when substantially water insoluble benefit agents are dispersed in water.

It has now been found that a liquid aqueous composition suitable for cleansing the skin and comprising a. a skin cleansing effective amount of a surfactant or mixtures thereof;

b. a silicone;

c. a hydrocarbonaceous material;

d. a cationic polymer; and e. the balance water can be successfully compatibilized by the addition of a combination of a hydroxy alkyl cellulose and a copolymer of a long chain alkylacrylate monomer and one or more monomers of acrylic acid, methacrylic acid and one or more of a methyl, ethyl or propyl ester of said acid(s) wherein the copolymer is cross linked with an allylic ether of a polyol.

Since neither one of these two compatibilizing agents alone stabilizes the composition at the quantities employed for each alone, there may be an unknown interaction occurring among the composition components. The usage of these two compatibility agents together bring about a composition which maintains visual phase integrity over a specific period of time and a wide temperature range. Additionally, the viscosity of the composition remains stable within reasonable tolerances over a specific period and a wide temperature range.

SUMMARY OF THE INVENTION

In accordance with the invention there is a liquid aqueous composition suitable for skin cleansing comprising a. a skin cleansing effective amount of a surfactant or mixture thereof;

b. a silicone in quantities of from about 0.1 to about 8 wt % of the composition;

c. a hydrocarbonaceous material in quantities of from about 0.1 to about 8 wt. % of the composition;

d. a cationic polymer in quantities of from about 0.02 to about 8 wt. % of the composition;

e. a combination of a hydroxy alkyl cellulose and a copolymer of a long chain alkylacrylate monomer and one or more monomers of acrylic acid, methacrylic acid and one or more of a methyl, ethyl or propyl ester of said acid(s) wherein the copolymer is cross linked with an allylic ether of a polyol, said combination in sufficient quantities to bring about a stabilized composition as visually evaluated; and f. the balance water.

The copolymer of e above has a viscosity of less than about 12,000, preferably less than about 10,000 centipoise as measured by a Brookfield RVTD viscometer at 25° C. using spindle 6 at 20 rpm on a 0.2 wt. % copolymer in deionized water adjusted to a pH of 5.9 with triethanolamine.

DETAILED DESCRIPTION OF THE INVENTION

In line with the cleansing activity of the composition, there must be a skin cleansing effective amount of a surfactant present in the composition. Soap, a long chain alkyl or alkenyl, branched or normal carboxylic acid salt such as sodium, potassium, ammonium or substituted ammonium salt, can be present in the composition. Exemplary of long chain alkyl or alkenyl are from about 8 to about 22 carbon atoms in length, specifically about 10 to about 20 carbon atoms in length, more specifically alkyl and most specifically normal, or normal with little branching. Small quantities of olefinic bond(s) may be present in the predominantly alkyl sections, particularly if the source of the "alkyl" group is obtained from a natural product such as tallow, coconut oil and the like. Because of its potential harshness soap is not a preferred surfactant and can be omitted from the composition.

Other surfactants can be present in the composition as well. Examples of such surfactants are the anionic, amphoteric, nonionic and cationic surfactants. Examples of anionic zwitterionic surfactants include but are not limited to alkyl sulfates, anionic acyl sarcosinates, methyl acyl taurates, N-acyl glutamates, acyl isethionates, alkyl sulfosuccinates, alkyl phosphate esters, ethoxylated alkyl phosphate esters, trideceth sulfates, protein condensates, mixtures of ethoxylated alkyl sulfates and the like.

Alkyl chains for these surfactants are $C_8$–$C_{22}$, preferably $C_{10}$–$C_{18}$, more preferably $C_{12}$–$C_{14}$.

Anionic non-soap surfactants can be exemplified by the alkali metal salts of organic sulfate having in their molecular structure an alkyl radical containing from about 8 to about 22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$–$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and others known in the art.

Zwitterionic surfactants can be exemplified by those which can be broadly described as derivatives of aliphatic quaternary ammonium, phosphonium, and sulfonium compounds, in which the aliphatic radicals can be straight chain or branched and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

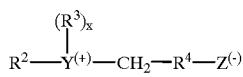

wherein $R^2$ contains an alkyl, alkenyl, or hydroxy alkyl radical of from about 8 to about 18 carbon atoms, from 0 to about 10 ethylene oxide moieties and from 0 to I glyceryl moiety; Y is selected from the group consisting of nitrogen, phosphorus, and sulfur atoms; R3 is an alkyl or monohydroxyalkyl group containing 1 to about 3 carbon atoms; X is I when Y is a sulfur atom and 2 when Y is a nitrogen or phosphorus atom, $R^4$ is an alkylene or hydroxyalkylene of from 0 to about 4 carbon atoms and Z is a radical selected from the group consisting of carboxylate, sulfonate, sulfate, phosphonate, and phosphate groups.

Examples include: 4-[N,N-di(2-hydroxyethyl)-N-octadecylammonio]-butane-1-carboxylate; 5-[S-3-hydroxypropyl-S-hexadecylsulfonio] -3 hydroxypentane-1-sulfate; 3-[P,P-P-diethyl-P 3,6,9 trioxatetradecyl-phosphonio]-2-hydroxypropane-1-phosphate; 3-[N,N-dipropyl-N-3 dodecoxy-2-hydroxypropylammonio]-propane-1-phosphonate; 3-(N,N-di-methyl-N-hexadecylammonio) propane-1-sulfonate; 3-(N,N-dimethyl-N-hexadecylammonio)-2-hydroxypropane-1-sulfonate; 4-(N,N-di(2-hydroxyethyl)-N-(2 hydroxydodecyl) ammonio]-butane-1-carboxylate; 3-[S-ethyl-S-(3-dodecoxy-2-hydroxypropyl)sulfonio]-propane-1-phosphate; 3-(P,P-dimethyl-P-dodecylphosphonio)-propane-1-phosphonate; and 5-[N,N-di(3-hydroxypropyl)-N-hexadecylammonio]-2-hydroxy-pentane-1-sulfate.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as the one prepared by reacting dodecylamine with sodium isethionate according to the teaching of U.S. Pat. No. 2,658,072, N-higher alkyl aspartic acids, such as those produced according to the teaching of U.S. Pat. No. 2,438,091, and the products sold under the trade name "Miranol" and described in U.S. Pat. No. 2,528,378. Other amphoterics such as betaines are also useful in the present composition.

Examples of betaines useful herein include the high alkyl betaines such as coco dimethyl carboxymethyl betaine, lauryl dimethyl carboxy-methyl betaine, lauryl dimethyl alpha-carboxyethyl betaine, cetyl dimethyl carboxymethyl betaine, lauryl bis-(2-hydroxyethyl)carboxy methyl betaine, stearyl bis-(2-hydroxypropyl) carboxymethyl betaine, oleyl dimethyl gamma-carboxypropyl betaine, lauryl bis-(2-hydro-xypropyl) alpha-carboxyethyl betaine, etc. The sulfobetaines may be represented by coco dimethyl sulfopropyl betaine, stearyl dimethyl sulfopropyl betaine, amido betaines, amidosulfobetaines, and the like.

Many cationic surfactants are known to the art. By way of example, the following may be mentioned:

stearyldimenthylbenzyl ammonium chloride;
dodecyltrimethylammonium chloride;
nonylbenzylethyldimethyl ammonium nitrate;
tetradecylpyridinium bromide;
laurylpyridinium chloride;
cetylpyridinium chloride
laurylpyridinium chloride;
laurylisoquinolium bromide;
ditallow(Hydrogenated)dimethyl ammonium chloride;
dilauryldimethyl ammonium chloride; and
stearalkonium chloride.

Additional cationic surfactants are disclosed in U.S. Pat. No. 4,303,543 see column 4, lines 58 and column 5, lines 1–42, incorporated herein by references. Also see CTFA Cosmetic Ingredient Dictionary, 4th Edition 1991, pages 509–514 for various long chain alkyl cationic surfactants; incorporated herein by references.

Nonionic surfactants can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration with ethylene oxide, e.g., a coconut alcohol ethylene oxide condensate having from 10 to 30 moles of ethylene oxide per mole of coconut alcohol, the coconut alcohol fraction having from 10 to 14 carbon atoms. Other ethylene oxide condensation products are ethoxylated fatty acid esters of polyhydric alcohols (e.g., Tween 20-polyoxyethylene (20) sorbitan monotaurate).

4. Long chain tertiary amine oxides corresponding to the following general formula:

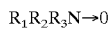

wherein $R_1$ contains an alkyl, alkenyl or monohydroxy alkyl radical of from about 8 to about 18 carbon atoms, from 0 to about 10 ethylene oxide moieties, and from 0 to 1 glyceryl moiety, and, $R_2$ and $R_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyldodecylamine oxide, oleyl-di(2-hydroxyethyl) amine oxide, dimethyloctylamine oxide, dimethyldecylamine oxide, dimethyltetradecylamine oxide, 3,6,9 trioxaheptadecyldiethylamine oxide, di(2-hydroxyethyl)-tetradecylamine oxide, 2-dodecoxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

wherein R contains an alkyl, alkenyl or monohydroxyalkyl radical ranging from 8 to 20 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecylmethylethylphosphine oxide, 3,6,9-trioxaoctadecyldimethylphosphine oxide, cetyldimethylphosphine oxide, 3-dodecoxy-2-hydroxypropyldi(2-hydroxyethyl) phosphine oxide stearyldimethylphosphine oxide, cetylethyl propylphosphine oxide, oleyldiethylphosphine oxide, dodecyldiethylphosphine oxide, tetradecyldiethylphosphine oxide, dodecyldipropylphosphine oxide, dodecyldi(hydroxymethyl)phosphine oxide, dodecyldi(2-hydroxyethyl)phosphine oxide, tetradecylmethyl-2-hydroxypropylphosphine oxide, oleyldimethylphosphine oxide, 2-hydroxydodecyldimethylphosphine oxide.

6. Long chain dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9-trioxaoctadecyl 2-hydroxyethyl sulfoxide, dodecyl methyl sulfoxide, oleyl 3-hydroxypropyl sulfoxide, tetradecyl methyl sulfoxide, 3 methoxytridecylmethyl sulfoxide, 3-hydroxytridecyl methyl sulfoxide, 3-hydroxy-4-dodecoxybutyl methyl sulfoxide.

7. Alkylated polyglycosides wherein the alkyl group is from about 8 to about 20 carbon atoms, preferably 10 to about 18 carbon atoms and the degree of polymerization of the glycoside is from about 1 to about 3, preferably about 1.3 to about 2.0.

Silicone as used herein is preferably a silicone fluid, as opposed to a silicone gum. A silicone fluid is defined herein as silicone with viscosities ranging from about 5 to about 600,000 centistokes, more preferably from about 350 to about 100,000 centistoke at 25° C. Polyalkyl siloxanes such as polydimethyl siloxane generally known as "dimethicone", are preferred for use as the silicone.

The silicone materials useful in the present invention are generally non-volatile and may be either a polyalkyl siloxane, a polyaryl siloxane, a polyalkylaryl, a functionalized siloxane, such as a polysiloxane with amino functional substitution, an alkoxylated silicone, such as ethoxylated or propoxylated, and a polyether siloxane copolymer. The silicones useful in the present invention may be endcapped with any number of moieties, including, for example, methyl, hydroxyl, ethylene oxide, propylene oxide, amino, trialkyl silane (preferably methyl), carboxyl, and the like, Mixtures of these materials may also be used and are preferred in certain implementations. Additionally, volatile silicones may be used as part of the silicone mixture so long as the final mixture is at least essentially non-volatile.

The polyalkyl silicones that may be used herein include, for example, polydimethyl siloxanes with viscosities ranging from about 5 to about 600,000 centistokes at 25° C. These siloxanes are available, for example, from General Electric Company as the Viscasil series and from Dow Corning as the Dow Corning 200 series. The viscosity can be measured by means of a glass capillary viscosmeter as set forth in Dow Corning Corporate Test Method CTM0004, Jul. 20, 1970. Preferably the viscosity ranges from about 50 centistokes to about 150,000 centistokes and most preferably from about 350 centistokes to about 100,000 centistokes.

The polyalkylaryl silicones that may be used include, for example, polymethylphenylsiloxanes having viscosities of from about 15 to about 65 centistokes at 25° C. These siloxanes are available, for example, from the General Electric Company as SF 1075 methyl phenyl fluid or from Dow Corning as 556 Cosmetic Grade Fluid. Additionally, poly(dimethyl siloxane) (diphenyl siloxane) copolymers having a viscosity in the range of from about 10 to about 100,000 centistokes at 25° C. are useful. The polyether siloxane copolymer that may be used is, for example, a polypropylene oxide modified dimethylpolysiloxane (e.g., Dow Corning DC-1248, although ethylene oxide or mixtures of ethylene oxide and propylene oxide may also be used.

References disclosing suitable silicones include U.S. Pat. No. 2,826,551, issued Mar. 11, 1958; Green; U.S. Pat. No. 3,964,500, issued Jun. 22, 1967, Drakoff, U.S. Pat. No. 4,364,837, issued Dec. 21, 1982, Pader; and British Patent No. 849,433, Wooston, published Sep. 28, 1960. All of these patents are incorporated herein by reference. Also incorporated herein by reference is Silicon Compounds, distributed by Petrarch Systems, Inc., 1984. This reference provides a good listing of suitable silicone material.

Component c can be a typical hydrocarbonaceous material such as a wax, petrolatum, mineral oil, beeswax, a "permethyl" made up of longer chain branched hydrocarbons available from Permethyl Corporation. Permethyls are of the general formula

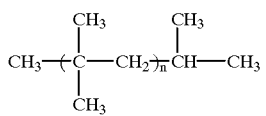

where n can vary from about 4 to over 200. Products where n=4, 16, 38, 214, respectively, are marketed as Permethyl 102A, 104A, 106A and 1082A.

Additional hydrocarbonaceous material which can be employed include lanolins and lanoleic like materials such as long chain alkyl esters and ethers of the lanolins.

The petrolatum useful in the present invention can be any grade of white or yellow petrolatum recognized in the art as suitable for human application. Preferred petrolatum are those with a melting point in a range of from about 35° C. to about 70° C., preferably about 50 to 60° C. The petrolatum of the composition can include hydrocarbon mixtures formulated with mineral oil and/or in combination with paraffin waxes of various melting points; all in small quantities compared to the petrolatum. A petrolatum without additional materials is preferred. Examples of waxes, particularly useful in solid compositions are microcrystalline waxes, generally those waxes which are known as paraffin wax, beeswax, and natural waxes derived from vegetables, shea wax and the like.

Cationic polymers is that generic class of materials which generally provide a positive skin feel to the skin during cleansing application, rinse off, and thereafter.

Cationic polymers includes but are not limited to the following groups:

(I) cationic polysaccharides;

(II) cationic copolymers of saccharides and synthetic cationic monomers, and (III) synthetic polymers selected from the group consisting of:
   (a) cationic polyalkylene imines
   (b) cationic ethoxy polyalkylene imines
   (c) cationic poly[N-[3-(dimethylammonio)propyl]-N' [3-(ethyleneoxyethylene dimethylammonio)propyl] urea dichloride]
   (d) in general a polymer having a quaternary ammonium or substituted ammonium ion.

The cationic polysaccharide class encompasses those polymers based on 5 or 6 carbon sugars and derivatives which have been made cationic by engraving of cationic moieties onto the polysaccharide backbone. They may be composed of one type of sugar or of more than one type, i.e. copolymers of the above derivatives and cationic materials. The monomers may be in straight chain or branched chain geometric arrangements. Cationic polysaccharide polymers include the following. cationic celluloses and hydroxyethylcelluloses; cationic starches and hydroxyalkyl starches; cationic polymers based on arabinose monomers such as those which could be derived from arabinose vegetable gums; cationic polymers derived from xylose polymers found in materials such as wood, straw, cottonseed hulls, and corn cobs, cationic polymers derived from fucose polymers found as a component of cell walls in seaweed; cationic polymers derived from fructose polymers such as Inulin found in certain plants; cationic polymers based on acid-containing sugars such as galacturonic acid and glucuronic acid; cationic polymers based on amine sugars such as galactosamine and glucosamine; cationic polymers based on 5 and 6 membered ring polyalcohols; cationic polymers based on galactose monomers which occur in plant gums and mucilages; cationic polymers based on mannose monomers such as those found in plants, yeasts, and red algae; cationic polymers based on galactommannan copolymer known as guar gum obtained from the endosperm of the guar bean.

Specific examples of members of the cationic polysaccharide class include the cationic hydroxyethyl cellulose JR 400 made by Union Carbide Corporation; the cationic starches Stalok® 100, 200, 300, and 400 made by Staley, Inc.; the cationic galactomannans based on guar gum of the Galactasol 800 series by Henkel, Inc. and the Jaguar Series by Celanese Corporation.

The cationic copolymers of saccharides and synthetic cationic monomers useful in the present invention encompass those containing the following saccharides: glucose, galactose, mannose, arabinose, xylose, fucose, fructose, glucosamine, galactosamine, glucuronic acid, galacturonic acid, and 5 or 6 membered ring polyalcohols. Also included are hydroxymethyl, hydroxyethyl and hydroxypropyl derivatives of the above sugars. When saccliarides are bonded to each other in the copolymers, they may be bonded via any of several arrangements, such as 1,4-α; 1,4-β; 1,3-α; 1,3-β and 1,6 linkages. The synthetic cationic monomers for use in these copolymers can include dimethyldiallylammonium chloride, dimethylaminoethylmethyacrylate, diethyldiallylammonium chloride, N,N-diallyl,N-N-dialklyl ammonium halides, and the like. A preferred cationic polymer is Polyquaternium 7 prepared with dimethyldiallylammonium chloride and acrylamide monomers.

Examples of members of the class of copolymers of saccharides and synthetic cationic monomers include those composed of cellulose derivatives (e.g. hydroxyethyl cellulose) and N,N-diallyl,N-N-dialkyl ammonium chloride available from National Starch Corporation under the tradename Celquat.

Further cationic synthetic polymers useful in the present invention are cationic polyalkylene imines, ethoxypolyalkelene imines, and poly{N-[3-(dimethylammonio)-propyl]-N'-[3-(ethyleneoxyethylene dimethylammoniumo)propyl]urea dichloride] the latter of which is available form Miranol Chemical Company, Inc. under the trademark of Miranol A-15, CAS Reg. No. 68555-336-2. Preferred cationic polymeric skin conditioning agents of the present invention are those cationic polysaccharides of the cationic guar gum class with molecular weights of 1,000 to 3,000,000. More preferred molecular weights are from 2,500 to 350,000. These polymers have a polysaccharide backbone comprised of galactomannan units and a degree of cationic substitution ranging from about 0.04 per anydroglucose unit to about 0.80 per anydroglucose unit with the substituent cationic group being the adduct of 2,3-epoxypropyl-trimethyl ammonium chloride to the natural polysaccharide backbone. Examples are JAGUAR C-14-S, C-15 and C-17 sold by Celanese Corporation, which trade literature reports have 1% viscosities of from 125 cps to about 3500±500 cps.

Still further examples of cationic polymers include the polymerized materials such as certain quaternary ammonium salts, copolymers of various materials such as hydroxyethyl cellulose and dialkyldimethyl ammonium chloride, acrylamide and beta methacryloxyethyl trimethyl ammonium methosulfate, the quaternary ammonium salt of methyl and stearyl dimethylamninoethyl methacrylate quaternized with dimethyl sulfate, quaternary ammonium polymer formed by the reaction of diethyl sulfate, a copolymer of vinylpyrrolidone and dimethyl aminoethylmethacrylate, quaternized guars and guar gums and the like. Exemplary of cationic polymers which can be used to make the complexes of this invention include, as disclosed in the CTFA International Cosmetic Ingredient Dictionary (Fourth Edition, 1991, pages 461–464); Polyquaternium -1, -2, -4 (a copolymer of hydroxyethylcellulose and diallyldimethyl ammonium chloride), -5 (the copolymer of acrylamide and beta-methacrylyloxyethyl trimethyl ammonium methosulfate), -6 (a polymer of dimethyl diallyl ammonium chloride), -7 (the polymeric quaternary ammonium salt of acrylamide and dimethyl diallyl ammonium chloride monomers, -8 (the polymeric quaternary ammonium salt of methyl and stearyl dimethylaminoethyl methacrylate quaternized with dimethyl sulfate), -9 (the polymeric quaternary ammonium salt of polydimethylaminoethyl methacrylate quaternized with methyl bromide), -10 (a polymeric quaternary ammonium salt of hydroxyethyl cellulose reacted with a trimethyl ammonium substituted epoxide), -11 (a quaternary ammonium polymer formed by the reaction of diethyl sulfate and a copolymer of vinyl pyrrolidone and dimethyl aminoethylmethacrylate), -12 (a polymeric quaternary ammonium salt prepared by the reaction of ethyl methacrylate/abietyl methacrylate/diethylaminoethyl methacrylate copolymer with dimethyl sulfate), -13 (a polymeric quaternary ammonium salt prepared by the reaction of ethyl methacrylate/oleyl methacrylate/diethylaminoethyl methacrylate copolymer with dimethyl sulfate), -14, -15 (the copolymer of acrylamide and betamethacrylyloxyethyl trimethyl ammonium chloride), -16 (a polymeric quaternary ammonium salt formed from methylvinylimidazolium chloride and vinylpyrrolidone), -17, -18, -19 (polymeric quaternary ammonium salt prepared by the reaction of polyvinyl alcohol with 2,3-epoxy-propylamine), -20 (the polymeric quaternary ammonium salt prepared by the reaction of polyvinyl octadecyl ether with 2,3-epoxypropylamine), -22, -24 a polymeric quaternary ammonium salt of hydroxyethyl cellulose reacted with a lauryl dimethyl ammonium substituted epoxide), -27 (the block copolymer formed by the reaction of Polyquaternium-2 (q.v.) with Polyquaternium-17 (q.v.)), -28, -29 (is Chitosan (q.v.) that has been reacted with propylene oxide and quaternized with epichlorohydrin), and -30.

The quantity of water present in the composition is substantial. Generally, at least about 60 wt % of the composition is water, usually at least about 70 wt %, and often times at least about 80 wt % of the composition is water. This large quantity of water together with a significant quantity of a difficult to solubilize organic like moiety such as silicone particularly together with the hydrocarbonaceous material, for example, petrolatum, creates a system which is highly unstable as measured by such parameters as visible examination of phases and viscosity.

Through the use of a combination of hydroxyalkylated methyl or non-methylated cellulose and a copolymer of a long chain alkyl acrylate and one or more monomers of acrylic acid, methacrylic acids or one or more of a methyl, ethyl or propyl ester of such acid(s) wherein the copolymer is cross-linked with an allylic ether of a polyol such as sucrose or pentaerythritol, the aqueous composition having both the silicone and the petrolatum is stabilized. Neither polymer alone appears to provide a stabilized composition. With respect to the cellulosic polymer, the alkylene group is two or three carbon atoms in length, preferably three, propyl. Methyl cellulose is preferred. With respect to the second polymer the long chain alkyl generally has a carbon chain of from about 8 to about 35 carbon atoms, preferably about 10 to about 30 carbon atoms. The polyol can have from about 4 to any maximum of hydroxyls but generally no more than about 12 can be readily incorporated into the copolymer, for example, about 10, preferably no more than about eight hydroxyls. Examples of polyols in addition to pentaerythritol and sucrose include glucose, mannose and fructose.

The surfactant level in the aqueous liquid composition is any level which can create foaming upon agitation when applied to the skin. Generally, this is a minimum of about 1 wt % of the composition, generally, at least about 2 wt % of the composition and preferably at least about 3, 4 or 5 wt % of the composition. Generally, not more than about 30 wt % of the composition is surfactant, although generally it is not more than about 25 or 20 wt % of the composition. Preferably, no more than about 17 wt % of the composition is surfactant. One or a mixture of surfactants can be employed. Generally, at least some of the surfactant is an anionic surfactant such as alkyl sulfate, ethoxylated alkyl sulfate, alpha olefin sulfonate or other mild surfactants, for example, taurates, phosphates and the like.

The quantity of silicone is generally from about 0.1 to about 8 wt % of the composition, preferably from about 0.5 to about 5 wt % of the composition.

The quantity of hydrocarbonaceous material is from about 0.1 to about 8 wt. % of the composition, preferably about 0.5 to abut 5 wt. %. The hydrocarbonaceous material is preferably a petrolatum as identified above. The particle size of the petrolatum can vary and is not unduly significant but is generally below about 20 microns, preferably below about 10 or even 5 microns as measured by an optical microscope of 200 power equipped with an image analyzer.

The cationic polymer is present from about 0.02 to about 1.0 wt. % of the composition, preferably about 0.05 to about 0.8 wt. % of the composition. Lower quantities can be employed, for example up to about 0.5 wt. % or up to about 0.4 wt. %.

The stability of the composition is maintained by the presence of the identified polymer systems previously identified, the hydroxyalkylated methyl or non-methylated cellulose and the copolymer of alkylacrylate or one or more monomers of acrylic acid, methacrylic acid or one or more of a methyl, ethyl or propylester of such acid(s) wherein the copolymer is cross-linked with an allylic ether of a polyol. Examples of the first polymer are the Methocel series (E, F, J, K) available from Dow Chemical and Viscontian MHPC available from Henkel. The propyl derivative, alkyl is three carbon atoms, is preferred. Examples of the second polymer are Pemulen TR-1 or Pemulen TR-2 preferably TR-1 available from Goodrich. Because the polymer is of an acidic nature, it is neutralized, or at least a portion of it, with a small amount of weak base such as amine compound, for example, triethanolamine. When measuring the viscosity in the manner disclosed earlier. Pemulen TR-1 has a viscosity of less than about 8000 and Pemulen TR-2 has a viscosity of less than about 2600. Generally a viscosity above about 1,000 is desirable. Carbopol 2020, a polymer that was ineffective in the compositions, had a viscosity of about 14,400 in the aforesaid test system The quantity of each of the polymer systems present in the composition is together sufficient to stabilize the system. Examples of stabilization parameter(s) include visual examination of the composition and viscosity, both with respect to time and temperature. Various combinations of quantities of the two polymer systems can be employed and it is somewhat difficult to fix absolute minima and maxima. However, in general, the first polymer (Methocel) is present in the composition at a minimum of about 0.1, or about 0.2, preferably about 0.3 wt % of the aqueous composition. The second polymer is present in the composition at a minimum of about 0.1 wt. % or about 0.2 wt. %, preferably about 0.3 wt % of the composition. As a general rule, the maximum quantities of the polymers are related to observable adverse effects present in the system such as too high a viscosity or, still further, when a smaller quantity of one polymer is used, in general a medium to relatively large quantity of the second polymer can be employed. However, in general, a maximum of about 1 wt. % preferably about 0.8 wt % of the composition of the first polymer can be employed. A maximum of about 1.0 preferably about 0.8 wt % of the composition of the second polymer can be employed.

In evaluating stability visually the key parameter is the maintenance of a single phase over the evaluated time and temperature range. With respect to viscosity, there can be some viscosity variation over the evaluated time and temperature range; however, this should be within normal expected and accepted variation for the desired viscosity. The viscosity of the composition should be one which is readily dispersible from a container by pouring, deforming the sides, or hand pumpable. Viscosity from about 1,000 to about 40,000 centipoise, preferably about 1,500 to about 30,000 centipoise can be employed. Viscosities up to about 20,000 are measured on a Brookfield RVT Viscometer using a number 5 spindle at 20 rpm and 25° C. Viscosities above about 20,000 centipoise are measured using a number 7 spindle at 20 rpm and 25° C.

Other thickeners, stabilizers, and emulsifiers have been placed into the composition and are unsuccessful in stabilizing this composition at an appropriate viscosity. These agents include long alkyl chain primary alcohols, ethoxylated or not having an average of from about 20 to about 40 carbon atoms. These materials are available from Perolite as Unilin and Unithox and have been successfully utilized to stabilize 2 in 1 conditioning hair shampoos having a silicone, dimethicone, therein. Even when the copolymer of the invention is added to the long chain alcohol containing composition, stability at an appropriate viscosity is not observed. Additionally, various polyacrylic polymers, specifically Ultrez 10, Carbopol 2020 and Carbopol 940 all available from Goodrich as part of its "Carbopol" series do not serve to appreciably thicken the composition of the invention when the copolymer of the invention is also present. Also, ineffective to provide stability and thicken the composition is Aculyn 33, an acrylic/acrylate copolymer. Additionally, ineffective as a stabilizer for the system was a typical thickener, a long chain ester, specifically PEG 150 stearate.

The composition of the invention appears to provide protection to the skin, even as a wash off product. Examples of such protection include but are not limited to less prevalence of a dye on the skin. Additionally, any fragrance present in the composition may be more longer lasting on the skin.

The compositions of the invention are made by standard techniques well known in the art. For example, various water soluble materials, such as the surfactant(s), cationic polymer(s), water soluble stabilizing polymer(s) are combined together with water, generally deionized, and mixed at an elevated temperature of about at least 50° C. preferably above about 85° C. The water insoluble materials are then mixed together in a separate vessel, for example, the petrolatum and water insoluble emollients if present and a free fatty acid if present at a similar elevated temperature. The water soluble and water insoluble materials are mixed at the elevated temperature for about fifteen minutes. The silicone is mixed with a nonionic surfactant if present and added to the other components at the elevated temperature and stirred an additional 15 minutes. The stabilizing cellulosic surface treated polymer is then contacted with an amine neutralizing agent in water to bring the pH to above 8. All the components are then mixed together at a temperature of about 50° C. for a period of time and other additional ingredients such as preservative and fragrance are added to about 40° C.

In the following comparison examples of the invention, as well as examples of the invention, the base composition below is employed:

12 wt % sodium laureth(2) sulfate
3 wt % cocoamidopropylbetaine
1.2 wt % decylpolyglycoside
0.2 wt % polyquat 7 active
various other components including emollient(s), preservatives and fragrances
water, q.s.

It should be noted that the surfactant system is not unique and various substitutions and eliminations can be made with respect to the surfactant system. In addition, the cationic polymer can also be changed and still have positive effects from the base compositions. The key components are the hydrocarbonaeous component and the silicone. In each of the ensuing examples, the hydrocarbonaeous component is petrolatum, specifically a white petrolatum having a melting point (range) of 50–60° C. available as Snow White Petrolatum from Penreco and the silicone is a dimethicone having a viscosity of 60,000 centistokes available as Viscasil-60M from General Electric.

Using the base composition previously mentioned together with 2 wt % petrolatum and 4 wt % dimethicone and 3 wt % of alkyl $C_{20-40}$ primary alcohol as well as Pemulen TR-1 at 0.3 wt % of the composition, various potential stabilizing materials are added to the composition at the following wt % of the composition. The results are observed.

| Comparative Example | Component, Wt % | Observation |
|---|---|---|
| 1 | None | Phase separation |
| 2 | Ultrez 10[a], 0.3 | Low viscosity |
| 3 | Carbopol 2020[b], 0.3 | Low viscosity |
| 4 | Carbopol 940[c], 0.3 | Low Viscosity |
| 5 | Carbopol 940, 0.5 | Some viscosity build-up |
| 6 | Carbopol 940, 0.75 | Some viscosity build-up |

[a]Ultrez is a polyacrylate available from Goodrich.
[b]Carbopol 2020 is acrylates/$C_{10-30}$ alkyl acrylate cross polymer available from Goodrich
[c]Carbopol 940 is a homopolymer of acrylic acid cross-linked with an alkyl ether of pentaerythritol or an alkyl ether of sucrose available from Goodrich.

Additional examples are prepared in the manner of the prior examples but without the long chain alkyl primary alcohol and without Pemulen TR[1], unless otherwise noted, and with 2 wt %, petrolium, and 1 wt % dimethicone. Additional potential stabilizing agents were added results observed:

| Comparative Example | Component Wt % | Observation |
|---|---|---|
| 7 | Pemulen, 0.3<br>PEG 150 Distearate, 0.3 | Separation after 2 weeks at 43.3° C. |
| 8 | Pemulen, 0.3<br>Methocel[d], 0.2<br>Crothix[e], 0.5 | High viscosity initially but did not hold. |
| 9 | Pemulen, 0.3<br>Methocel, 0.35 | Phase separation after 8 weeks at 43.3° F. |
| 10 | Aculyn 33[f], 4 | Separated at 2 weeks, 43.3° C. |
| 11 | Methocel, 0.25<br>Aculyn, 4 | Separation at 4 weeks at 48.8° C. |
| 12 | Methocel, 0.25<br>Aculyn, 5 | Separation and low viscosity upon aging |
| 13 | Methocel, 0.5<br>Aculyn, 4 | Separation after 2 weeks at 48.8° C. |

[d]Methocel is hydroxypropylmethyllcellulose available from Dow.
[e]Crothix is PEG-150 pentaerythrityl tetrastearate available from Croda.
[f]Aculyn 33 is a an acrylic/acrylate copolymer available from Rohm & Haas, 28% active.

Following the procedure for comparative examples 7–13 and utilizing the same wt % of components employed, further evaluations are performed.

| Comparative Example | Component Wt % | Observation |
|---|---|---|
| 14* | Pemulen, 0.3 | Separated after 2 weeks at 43.3° C. |
| 15 | Pemulen, 0.3 Methocel, 0.35 | Separation after 2 weeks at 43.3° C. |
| 16 | Pemulen, 0.2 Methocel, 0.7 | Separation after 2 weeks at 43.3° C. |

*2 wt. % petrolatum and 2 wt. % dimethicone

These experiments show that Pemulen alone does not stabilize the system and that Methocel does not provide stabilization to a Pemulen containing composition if there is insufficient Methocel present or insufficient Pemulen present.

Below is an example illustrating the invention. This example is intended to illustrate the broad inventive scope and not unduly limit the invention. The petrolatum is at 2 wt % and the dimethicone is 1 wt % or 4 wt % in two different compositions.

| Example | Component Wt % | Observation |
|---|---|---|
| 1 | Pemulen, 0.3 Methocel, 0.7 | Appropriate viscosity and phase stability at 43.3° C. for at least 12 weeks. |

A surface treated hydroxy propyl methyl cellulose available from Dow as Methocel 40–202 is generally preferred for its ease of handling in preparation of the compositions.

A further composition which is now being employed comprises 7.6 wt. % sodium laureth (2) sulfate, 2.1 wt. % cocoamidopropylbetaine, 0.6 wt. % decylpolyglucoside dp 1.4, 1 wt. % dimethicone, 2 wt. % petrolatum, 0.2 wt. % active polyquat-7, 0.5 wt. % Methocel E4M, a non-surface coated hydroxypropyl methyl cellulose, and 0.5 wt. % Pemulen TR1, the remainder essentially water.

These examples, comparative and working, clearly emphasize and illustrate the unique features of the invention.

What is claimed is:

1. A liquid aqueous composition comprising:
   (a) a skin cleansing effective amount of a surfactant or mixture thereof;
   (b) a silicone fluid in quantities of from about 0.1 to about 8 wt % of the composition;
   (c) a hydrocarbonaceous material in quantities of from about 0.1 to about 8 wt % of the composition;
   (d) a cationic polymer in quantities of from about 0.02 to about 1 wt % of the composition;
   (e) a combination of a hydroxy alkyl cellulose and a copolymer of a long chain alkylacrylate monomer and one or more monomers of acrylic acid, methacylic acid and one or more of a methyl, ethyl or propyl ester of said acid(s) wherein the copolymer is crosslinked with an allylic ether of a polyol, said combination in sufficient quantities to bring about a stabilized composition as visually evaluated, and the copolymer has a viscosity of less than about 12,000 as measured on a Brookfield RVTD viscometer at 25° C. using spindle 6 at 20 rpm on a 0.2 wt. % copolymer in deionized water at a pH of 5.9 as adjusted with triethanolamine; and
   f. the remainder water.

2. The composition in accordance with claim 1 wherein in (e) the hydroxyl alkyl cellulose is at least about 0.1 wt. % of the composition and the said copolymer is at least about 0.1 wt. % of the composition.

3. The composition in accordance with claim 2 wherein the said alkyl of the cellulose is two or three carbon atoms.

4. The composition in accordance with claim 2 wherein the said alkyl is three carbon atoms.

5. The composition in accordance with claim 1 wherein (a) is at least about 1 wt. % of the composition.

6. The composition in accordance with claim 1 wherein (b) is from about 0.5 to about 5 wt. %.

7. The composition in accordance with claim 1 wherein (c) is from about 0.5 to abut 5 wt. %.

8. The composition in accordance with claim 1 wherein (d) is from about 0.05 to abut 0.8 wt. %.

9. The composition in accordance with claim 5 wherein an anionic surfactant is present.

10. The composition in accordance with claim 6 wherein (b) is a dimethyl silicone.

11. The composition in accordance with claim 7 wherein (c) is a petrolatum.

12. The composition in accordance with claim 8 wherein (d) is polyqauaterium 6, polyquaternium 7 or a mixture thereof.

13. The composition in accordance with claim 2 wherein the cellulose is a methyl cellulose.

14. The composition in accordance with claim 3 wherein the cellulose is a methyl cellulose.

15. The composition in accordance with claim 4 wherein the cellulose is a methyl cellulose.

16. The composition in accordance with claim 1, wherein the composition has visual phase integrity at 43.3° C. for at least 12 weeks.

17. The composition in accordance with claim 1, wherein the composition has visual phase integrity at 43.3° C. for at least 12 weeks.

* * * * *